(12) United States Patent
Chen

(10) Patent No.: US 9,581,563 B2
(45) Date of Patent: *Feb. 28, 2017

(54) SYSTEM FOR COMMUNICATING INFORMATION FROM AN ARRAY OF SENSORS

(75) Inventor: Roger Chen, Saratoga, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 1165 days.

This patent is subject to a terminal disclaimer.

(21) Appl. No.: 13/272,109

(22) Filed: Oct. 12, 2011

(65) Prior Publication Data

US 2012/0188092 A1     Jul. 26, 2012

Related U.S. Application Data

(60) Provisional application No. 61/435,700, filed on Jan. 24, 2011.

(51) Int. Cl.
*G08C 15/06* (2006.01)
*G01N 27/327* (2006.01)
*G01N 33/487* (2006.01)

(52) U.S. Cl.
CPC ... *G01N 27/3278* (2013.01); *G01N 33/48721* (2013.01)

(58) Field of Classification Search
CPC ............. Y10T 307/826; Y10T 307/858; Y10T 307/865; G01N 27/3278; G01N 33/48721
USPC ........................................ 307/125, 130, 131
See application file for complete search history.

(56) References Cited

U.S. PATENT DOCUMENTS

| | | | |
|---|---|---|---|
| 2,656,508 A | 10/1953 | Coulter |
| 3,638,120 A | 1/1972 | Jost |
| 4,121,192 A | 10/1978 | Wilson |
| 4,713,347 A | 12/1987 | Mitchell et al. |
| 4,859,945 A | 8/1989 | Stokar |
| 5,021,692 A | 6/1991 | Hughes |
| 5,198,543 A | 3/1993 | Blanco et al. |
| 5,260,663 A | 11/1993 | Blades |

(Continued)

FOREIGN PATENT DOCUMENTS

CN     101421616     4/2009
EP     1236807     11/1998

(Continued)

OTHER PUBLICATIONS

Osaki et al., Analytical Chemistry, vol. 81, No. 24, pp. 9866-9870, Dec. 15, 2009.

(Continued)

*Primary Examiner* — Fritz M Fleming
(74) *Attorney, Agent, or Firm* — Van Pelt, Yi & James LLP

(57) ABSTRACT

A system for communicating information from an array of sensors is disclosed. The system comprises a sensor array that includes a plurality of sensors, wherein each sensor senses a physical property of a material that is in communication with the sensor. The system further comprises signal processing circuitry associated with each sensor that integrates the output of the sensor over time and compares the integrated output to a threshold. The system further comprises a communication network coupled to the signal processing circuitry that outputs information indicating that the integrated output corresponding to a given sensor has reached the threshold.

17 Claims, 6 Drawing Sheets

(56) References Cited

U.S. PATENT DOCUMENTS

| | | |
|---|---|---|
| 5,302,509 A | 4/1994 | Cheeseman |
| 5,308,539 A | 5/1994 | Koden et al. |
| 5,457,342 A | 10/1995 | Herbst, II |
| 5,569,950 A | 10/1996 | Lewis et al. |
| 5,576,204 A | 11/1996 | Blanco et al. |
| 5,747,805 A | 5/1998 | Youngquist |
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju |
| 5,814,454 A | 9/1998 | Ju |
| 5,869,244 A | 2/1999 | Martin et al. |
| 5,876,936 A | 3/1999 | Ju |
| 5,912,155 A | 6/1999 | Chatterjee et al. |
| 5,939,301 A | 8/1999 | Hughes, Jr. et al. |
| 5,952,180 A | 9/1999 | Ju |
| 5,981,733 A | 11/1999 | Gamble et al. |
| 6,012,291 A | 1/2000 | Ema |
| 6,014,213 A | 1/2000 | Waterhouse et al. |
| 6,015,714 A | 1/2000 | Baldarelli et al. |
| 6,046,005 A | 4/2000 | Ju et al. |
| 6,082,115 A | 7/2000 | Strnad |
| 6,210,896 B1 | 4/2001 | Chan |
| 6,217,731 B1 | 4/2001 | Kane et al. |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,321,101 B1 | 11/2001 | Holmstrom |
| 6,362,002 B1 | 3/2002 | Denison et al. |
| 6,383,749 B2 | 5/2002 | Bochkariov et al. |
| 6,399,320 B1 | 6/2002 | Markau et al. |
| 6,399,335 B1 | 6/2002 | Kao et al. |
| 6,413,792 B1 | 7/2002 | Sauer |
| 6,485,703 B1 | 11/2002 | Cote et al. |
| 6,607,883 B1 | 8/2003 | Frey et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,686,997 B1 | 2/2004 | Allen |
| 6,699,719 B2 | 3/2004 | Yamazaki et al. |
| 6,723,513 B2 | 4/2004 | Lexow |
| 6,746,594 B2 | 6/2004 | Akeson et al. |
| 6,762,048 B2 | 7/2004 | Williams |
| 6,794,177 B2 | 9/2004 | Markau et al. |
| 6,800,933 B1 | 10/2004 | Mathews et al. |
| 6,824,659 B2 | 11/2004 | Bayley et al. |
| 6,880,346 B1 | 4/2005 | Tseng et al. |
| 6,891,278 B2 | 5/2005 | Mulleret et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,368,668 B2 | 5/2008 | Ren et al. |
| 7,405,281 B2 | 7/2008 | Xu et al. |
| 7,410,564 B2 | 8/2008 | Flory |
| 7,446,017 B2 | 11/2008 | Liu et al. |
| 7,452,698 B2 | 11/2008 | Sood et al. |
| 7,622,934 B2 | 11/2009 | Hibbs et al. |
| 7,625,701 B2 | 12/2009 | Williams et al. |
| 7,626,379 B2 | 12/2009 | Peters et al. |
| 7,710,479 B2 | 5/2010 | Nitta et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,871,777 B2 | 1/2011 | Schneider et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,324,914 B2 | 12/2012 | Chen et al. |
| 8,461,854 B2 | 6/2013 | Chen et al. |
| 8,828,208 B2 | 9/2014 | Canas et al. |
| 8,962,242 B2 * | 2/2015 | Chen .......................... 435/6.1 |
| 2002/0039743 A1 | 4/2002 | Hashimoto et al. |
| 2003/0027140 A1 | 2/2003 | Ju et al. |
| 2003/0054360 A1 | 3/2003 | Gold et al. |
| 2003/0080042 A1 | 5/2003 | Barth et al. |
| 2003/0101006 A1 | 5/2003 | Manksy et al. |
| 2003/0102263 A1 | 6/2003 | Lopez et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0144658 A1 | 7/2004 | Flory |
| 2004/0185466 A1 | 9/2004 | Ju et al. |
| 2004/0262636 A1 | 12/2004 | Yang et al. |
| 2005/0032081 A1 | 2/2005 | Ju et al. |
| 2005/0091989 A1 | 5/2005 | Leija et al. |
| 2005/0127035 A1 | 6/2005 | Ling |
| 2005/0136408 A1 | 6/2005 | Tom-Moy et al. |
| 2005/0164286 A1 | 7/2005 | O'uchi et al. |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239194 A1 | 10/2005 | Takahashi et al. |
| 2006/0057565 A1 | 3/2006 | Ju et al. |
| 2006/0057585 A1 | 3/2006 | McAllister |
| 2006/0105461 A1 | 5/2006 | Tom-Moy et al. |
| 2006/0246497 A1 | 11/2006 | Huang et al. |
| 2006/0252038 A1 | 11/2006 | Ju |
| 2006/0278992 A1 | 12/2006 | Trezza et al. |
| 2007/0173731 A1 | 7/2007 | Meka et al. |
| 2007/0190542 A1 | 8/2007 | Ling et al. |
| 2007/0191015 A1 | 8/2007 | Hwang et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0171316 A1 | 7/2008 | Golovchenko et al. |
| 2008/0199932 A1 | 8/2008 | Hanzel et al. |
| 2008/0217546 A1 * | 9/2008 | Steadman et al. ........ 250/370.09 |
| 2008/0218184 A1 | 9/2008 | White et al. |
| 2008/0254995 A1 | 10/2008 | Kim et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167228 A1 | 7/2009 | Chung et al. |
| 2009/0167288 A1 | 7/2009 | Reid et al. |
| 2009/0215050 A1 | 8/2009 | Jenson |
| 2009/0233280 A1 | 9/2009 | Nomoto et al. |
| 2009/0269759 A1 | 10/2009 | Menchen et al. |

(56) References Cited

U.S. PATENT DOCUMENTS

| | | |
|---|---|---|
| 2009/0298072 A1 | 12/2009 | Ju |
| 2010/0025238 A1 | 2/2010 | Gottlieb et al. |
| 2010/0025249 A1 | 2/2010 | Polonksy et al. |
| 2010/0035260 A1 | 2/2010 | Olasagati et al. |
| 2010/0047802 A1 | 2/2010 | Bjornson et al. |
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078325 A1 | 4/2010 | Oliver |
| 2010/0078777 A1 | 4/2010 | Barth et al. |
| 2010/0084276 A1 | 4/2010 | Lindsay |
| 2010/0092952 A1 | 4/2010 | Ju et al. |
| 2010/0093555 A1 | 4/2010 | Bjornson et al. |
| 2010/0121582 A1 | 5/2010 | Pan et al. |
| 2010/0122907 A1 | 5/2010 | Standford et al. |
| 2010/0148126 A1 | 6/2010 | Guan et al. |
| 2010/0196203 A1 | 8/2010 | Sanghera et al. |
| 2010/0243449 A1 | 9/2010 | Oliver |
| 2010/0261247 A1 | 10/2010 | Hanzel et al. |
| 2010/0261287 A1 | 10/2010 | Holt et al. |
| 2010/0292101 A1 | 11/2010 | So |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0008775 A1 | 1/2011 | Gao et al. |
| 2011/0050200 A1 | 3/2011 | Tartagni et al. |
| 2011/0053284 A1 | 3/2011 | Meller et al. |
| 2011/0059505 A1 | 3/2011 | Hanzel et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0226623 A1 | 9/2011 | Timp et al. |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040343 A1 | 2/2012 | Timp et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0133354 A1 | 5/2012 | Canas et al. |
| 2012/0149021 A1 | 6/2012 | Yung et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2012/0322679 A1 | 12/2012 | Brown et al. |
| 2013/0015068 A1 | 1/2013 | Chen et al. |
| 2013/0071837 A1 | 3/2013 | Winters-Hilt et al. |
| 2013/0118902 A1 | 5/2013 | Akeson et al. |
| 2013/0207205 A1 | 8/2013 | Chen |
| 2013/0244340 A1 | 9/2013 | Davis et al. |
| 2013/0263946 A1 | 10/2013 | Afzali-Ardakani et al. |
| 2013/0327644 A1 | 12/2013 | Turner et al. |
| 2014/0034497 A1 | 2/2014 | Davis et al. |
| 2014/0296083 A1 | 10/2014 | Brown et al. |
| 2014/0329693 A1 | 11/2014 | Reid et al. |
| 2014/0346059 A1 | 11/2014 | Akeson et al. |

FOREIGN PATENT DOCUMENTS

| | | |
|---|---|---|
| JP | 2004205495 | 7/2004 |
| JP | 2004333485 | 11/2004 |
| JP | 2005538377 | 12/2005 |
| JP | 2008507703 | 3/2008 |
| JP | 2010502936 | 1/2010 |
| JP | 2010524436 | 7/2010 |
| JP | 2011506994 | 3/2011 |
| JP | 2012026986 | 2/2012 |
| JP | 2013512447 | 4/2013 |
| WO | 91/06678 | 5/1991 |
| WO | 93/21340 | 10/1993 |
| WO | 97/32999 | 9/1997 |
| WO | 97/46704 | 12/1997 |
| WO | 02/22883 | 3/2002 |
| WO | 02/29003 | 4/2002 |
| WO | 02/079519 | 10/2002 |
| WO | 2004/007773 | 1/2004 |
| WO | 2004/055160 | 7/2004 |
| WO | 2005/084367 | 9/2005 |
| WO | 2006/020775 | 2/2006 |
| WO | 2007/002204 | 1/2007 |
| WO | 2007/053702 | 5/2007 |
| WO | 2007/053719 | 5/2007 |
| WO | 2007/062105 | 5/2007 |
| WO | WO-2007115694 | 10/2007 |
| WO | 2007/127327 | 11/2007 |
| WO | 2007/146158 | 12/2007 |
| WO | 2008/034602 | 3/2008 |
| WO | 2008/069973 | 6/2008 |
| WO | 2008071982 | 6/2008 |
| WO | WO-2008079169 | 7/2008 |
| WO | 2008/102120 | 8/2008 |
| WO | 2008/124107 | 10/2008 |
| WO | 2009/051807 | 4/2009 |
| WO | WO-2009047703 | 4/2009 |
| WO | WO-2009077734 | 6/2009 |
| WO | 2009138760 | 11/2009 |
| WO | WO-2010044932 | 4/2010 |
| WO | 2010122293 | 10/2010 |
| WO | 2011/097028 | 8/2011 |
| WO | 2011103424 | 8/2011 |
| WO | 2011/106459 | 9/2011 |
| WO | 2012/009578 | 1/2012 |
| WO | 2012/088339 | 6/2012 |
| WO | 2012/088341 | 6/2012 |
| WO | 2012/121756 | 9/2012 |
| WO | 2013011879 | 1/2013 |
| WO | 2013082619 | 6/2013 |

OTHER PUBLICATIONS

Mosquera et al., Thermal Decomposition and Fractal Properties of Sputter-Deposited Platinum Oxide Thin Films, Journal of of Materials Research, pp. 829-836, Mar. 14, 2012.

Jetha et al., Chapter 9, Forming an a-Hemolysin Nanopore for Single-Molecule Analysis from Micro and Nano Technologies in Bioanlysis, Methods in Molecular Biology, vol. 544, pp. 113-127, 2009.

Jiang et al., Chapter 14, Passive and Electrically Actuated Solid-State Nanopores for Sensing and Manipulating DNA from Nanopore-Based Technology, Methods in Molecular Biology, vol. 870, pp. 241-264, 2012.

Kim et al., Advanced Materials, Rapid Fabrication of Uniformly Sized Nanopres and Nanopore Arrays for Parallel DNA Analysis, vol. 18, pp. 3149-3153, 2006.

WP Thompson LTR May 28, 2013.

Author Unknown, Low Noise, Dual Switched Integrator, Burr-Brown Corporation, Sep. 1994.

Author Unknown, Oxford Nanopore Technologies, Sensor Array Chip, Jul. 14, 2011.

U.S. Appl. No. 61/170,729, filed Apr. 20, 2009.

Mollazadeh et al. "Micropower CMOS integrated low-noise amplification, filtering, and digitization of multimodal neuropotentials." Biomedical Circuits and Systems, IEEE Transactions on 3.1 (2009): 1-10.

Akeson, et al. Microsecond time-scale discrimination among polycytidylic acid, polyadenylic acid, and plolyuridylic acid as homopolymers or a s segments within single RNA molecules. Biophys J. Dec. 1999; 77(6):3227-33.

(56) References Cited

OTHER PUBLICATIONS

Aksimentiev, et al. Microscopic Kinetics of DNA Translocation through synthetic nanopores. Biophys J. Sep. 2004;87(3):2086-97.
Andersen. Sequencing and the single channel. Biophys J. Dec. 1999; 77(6):2899-901.
Ashkenasy, et al. Recognizing a single base in an individual DNA strand: a step toward DNA sequencing in nanopores. Angew Chem Int Ed Engl. Feb. 18, 2005:44(9):1401-4.
Atanasov, et al. Membrane on a chip: a functional tethered lipid bilayer membrane on silicon oxide surfaces. Biophys J. Sep. 2005;89(3):1780-8.
Baaken, et al. Planar microelecrode-cavity array for hig-resolution and parallel electrical recording of membrane ionic currents. Lab Chip. Jun. 2008;8(6):938-44. Epub Apr. 16, 2008.
Bai, et al. Design and synthesis of a photocleavable biotinylated nucleotide for DNA analysis by mass spectrometry. Nucleic Acids Res. Jan. 26, 2004;32(2):535-41. Print 2004.
Benner, et al. Sequence-specific detection of individual DNA polymerase complexes in real time using a nanopore. Nat Nanotechnol. Nov. 2007;2(11):718-24. Epub 200 Oct. 28.
Bezrukov, et al. Counting polymers moving through a single ion channel. Nature. Jul. 28, 1994;370(6487):279-81.
Bezrukov, et al. Dynamic partitioning of neutral polymers into a single ion channel. In NATO Advanced Research Workshop: Structure and dynamics of confined polymers. Kulwer Press. 2002; 117-130.
Bezrukov, et al. Dynamics and free energy of polymers partitioning into a nanoscale pore. Macromolecules. 1996; 29:8517-8522.
Bezrukov, et al. Neutral polymers in the nanopores of alamethicin and alpha-hemolysin. Biologicheskie Membrany 2001, 18, 451-455.
Boireau, et al. Unique supramolecular assembly of a redox protein with nucleic acids onto hybrid bilayer: towards a dynamic DNA chip. Biosens Bioelectron. Feb. 15, 2005;20(8):1631-7.
Bokhari, et al. A parallel graph decomposition algorithm for DNA sequencing with nanopores. Bioinformatics. Apr. 1, 2005;21(7):889-96. Epub Nov. 11, 2004.
Buchmann, et al. Electrochemical release from gold-thiolate electrodes for controlled insertion of ion channels into bilayer membranes. Bioorg Med Chem. Mar. 15, 2004;12(6):1315-24.
Butler et al. of RNA orientation during translocation through a biological nanopore. Biophys J. Jan. 1, 2006;90(1):190-9. Epub Oct. 7, 2005.
Butler et al. Single-molecule DNA detection with an engineered MspA protein nanopore. Proc Natl Acad Sci U S A. Dec. 30, 2008;105(52):20647-52. Epub Dec. 19, 2008.
Butler, et al. Ionic current blockades from DNA and RNA molecules in the alphahemolysis nanopore. Biophys J. Nov. 1, 2007;93(9):3229-40. Epub Aug. 3, 2007.
Chandler, et al. Membrane surface dynamics of DNA-threaded nanopores revealed by simultaneous single-molecule optical and ensemble electrical recording. Langmuir. Feb. 3, 2004;20(3):898-905.
Churbanov, et al. Duration learning for analysis of nanopore ionic current blockades. BMC Bioinformatics. Nov. 1, 2007;8 Suppl 7:S14.
Clarke, et al. Continuous base identification for single-molucule nanpore DNA sequencing. Nat Nanotechnol. Apr. 2009;4(4):265-70. Epub Feb. 22, 2009.
Cockroft, et al. A single-molecule nanpore device detects DNA polymerase activity with single-nucleotide resolution. J am Chem Soc. Jan. 23, 2008;130(3):818-20. Epub Jan. 1, 2008.
Danelon, et al. Cell membranes suspended across nanoaperture arrays. Langmuir. Jan. 3, 2006;22(1):22-5.
Deamer, et al. Characterization of nucleic acids by nanopore analysis. Acc Chem Res. Oct. 2002;35(10):817-25.
Derrington, et al. Nanopore DNA sequencing with MspA. Proc Natl Acad Sci U S A. Sep. 14, 2010;107(37):16060-5. Epub Aug. 26, 2010.

Einstein. Investigations on the theory of Brownian movement. Dover, New York. 1956.
Ervin, et al. Simultaneous alternating and direct current readout of protein ion channel blocking events using glass nanopore membranes. Anal Chem. Mar. 15, 2008;80(6):2069-76. Epub Feb. 23, 2008.
Flusberg, et al. Direct detection of DNA methylation during single-molecule, real-time sequencing. Nat Methods. Jun. 2010;7(6):461-5. Epub May 9, 2010.
Fologea, et al. Detecting single stranded DNA with a solid state nanopore. Nano Lett. Oct. 2005;5(10):1905-9.
Fologea, et al. Slowing DNA translocation in a solid-state nanopore. Nano Lett. Sep. 2005;5(9):1734-7.
Gu, et al. Stochastic sensing of organic analytes by a pore-forming protein containing a molecular adapter. Nature. Apr. 22, 1999;398(6729):686-90.
Haas, et al. Improvement of the qualiity of self assembled bilayer lipid membranes by using a negative potential. Bioelectrochemistry. Aug. 2001;54(1):1-10.
Halverson, et al. Asymmetric blockade of anthrax protective antigen ion channel asymmetric blockade. J Biol Chem. Oct. 7, 2005;280(40):34056-62. Epub Aug. 8, 2005.
Harlepp, et al. Probing complex RNA structures by mechanical force. Eur Phys J E Soft Matter. Dec. 2003;12(4):605-15.
Heins, et al. Detecting single porphyrin molecules in a conically shaped synthetic nanopore. Nano Lett. Sep. 2005;5(9):1824-9.
Heng, et al. Stretching DNA using the electric field in a synthetic nanopore. Nano Lett. Oct. 2005;5(10):1883-8.
Heng, et al. The electromechanics of DNA in a synthetic nanopore. Biophys J. Feb. 1, 2006;90(3):1098-106. Epub Nov. 11, 2005.
Henrickson, et al. Driven DNA transport into an asymmetric nanometer-scale pore. Phys Rev Lett. Oct. 2, 2000;85(14):3057-60.
Henrickson, et al. Probing single nanometer-scale pores with polymeric molecular rulers. J Chem Phys. Apr. 7, 2010;132(13):135101. doi: 10.1063/1.3328875.
Holden, et al. Direct introduction of single protein channels and pores into lipid bilayers. J Am Chem Soc. May 11, 2005;127(18):6502-3.
Holden, et al. Direct transfer of membrane proteins from bacteria to planar bilayers for rapid screening by single-channel recording. Nat Chem Biol. Jun. 2006;2(6):314-8. Epub May 7, 2006.
Hromada, et al. Single molecule measurements within individual membrane-bound ion channels using a polymer-based bilayer lipid membrane chip. Lab Chip. Apr. 2008;8(4):602-8. Epub Feb. 29, 2008.
International Preliminary Report on Patentability issued Dec. 24, 2008 in connection with International Application No. PCT/US2007/013559.
International search report and written opinion dated Mar. 18, 2013 for PCT/US2012/063099.
International search report and written opinion dated May 3, 2012 for PCT/US2012/020827.
International search report and written opinion dated May 9, 2013 for PCT/US2013/028058.
International search report and written opinion dated May 16, 2013 for PCT Application No. US2013/022273.
International search report and written opinion dated May 16, 2013 for PCT Application No. US2013/026514.
International search report and written opinion dated Jul. 8, 2011 for PCT/US2011/064490.
International search report and written opinion dated Aug. 28, 2012 for PCT/US2011/066627.
International search report and written opinion dated Aug. 28, 2012 for PCT/US2011/066632.
International search report and written opinion dated Oct. 29, 2007 for PCT/US2007/013559.
International search report and written opinion dated Nov. 5, 2012 for PCT/US2011/064490.
International search report dated Feb. 24, 2013 for PCT/US2011/065640.
Ito, et al. Simultaneous determination of the size and surface charge of individual nanoparticles using a carbon nanotube-based Coulter counter. Anal Chem. May 15, 2003;75(10)2399-406.

(56) References Cited

OTHER PUBLICATIONS

Ju, et al. Cassette labeling for facile construction of energy transfer fluorescent primers. Nucleic Acids Res. Mar. 15, 1996;24(6):1144-8.
Ju, et al. Energy transfer primers: a new fluorescence labeling paradigm for DNA sequencing and analysis. Nat Med. Feb. 1996;2(2):246-9.
Ju, et al. Fluorescence energy transfer dye-labeled primers for DNA sequencing and analysis. Proc Natl Acad Sci U S A. May 9, 1995;92(10):4347-51.
Ju, et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jurak, et al. Wettability and topography of phospholipid DPPC multilayers deposited by spin-coating on glass, silicon and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Kasianowicz, et al. Characterization of individual polynucleotide molecules using a membrane channel. Proc Natl Acad Sci U S A. Nov. 26, 1996;93(24):13770-3.
Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.
Kasianowicz, et al. Simultaneous multianalysis detection with a nanopore. Anal. Chem. 2001; 73:2268-2272.
Kasianowicz. Nanometer-scale pores: potential applications for analyte detection and DNA characterization. Dis Markers. 2002;18(4):185-91.
Kasianowicz. Nanopores: flossing with DNA. Nat Mater. Jun. 2004;3(6):355-6.
Kawano, et al. Controlling the translocation of single-stranded DNA through alphahemolysin ion channels using viscosity. Langmuir. Jan. 20, 2009;25(2):1233-7.
Krasilnikov, et al. A simple method for the determination of the pore radius of ion channels in planar lipid bilayer membranes. FEMS Microbiol Immunol. Sep. 1992;5(1-3):93-100.
Krasilnikov, et al. Single polymer molecules in a protein nanopore in the limit of a strong polymer-pore attraction. Phys Rev Lett. Jul. 7, 2006;97(1):018301. Epub Jul. 5, 2006.
Krasilnikov, et al. Sizing channels with neutral polymers. In NATO Advanced Research Workshop: Structure and dynamics of confined polymers. Kluwer Press. 2002; 97-116.
Kullman, et al. Transport of maltodextrins through maltoporin: a single-channel study. Biophys J. Feb. 2002;82(2):803-12.
Kumar, et al. PEG-labeled nucleotides and nanopore detection for single molecule DNA sequencing by synthesis. Sci Rep. 2012;2:684. Epub Sep. 21, 2012.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7):1565-73.
Li, et al. A photocleavable fluorescent nucleotide for DNA sequencing and analysis. Proc Natl Acad Sci U S A. Jan. 21, 2003;100(2):414-9. Epub Jan. 6, 2003.
Li, et al. Ion-beam sculpting at nanometre length scales. Nature. Jul. 12, 2001;412(6843):166-9.
Linear Technology, High Efficiency Thermoelectric Cooler Controller, 2001.
Low Noise, Dual Switched Integrator, Burr-Brown Corporation, Sep. 1994.
Lundquist, et al. A new tri-orthogonal strategy for peptide cyclization. Org Lett. Sep. 19, 2002;4(19):3219-21.
Madampage, et al. Nanopore detection of antibody prion interactions. Anal Biochem. Jan. 1, 2010;396(1):36-41. Epub Aug. 21, 2009.
Mathe, et al. Nanopore unzipping of individual DNA hairpin molecules. Biophys J. Nov. 2004;87(5):3205-12. Epub Sep. 3, 2004.
Mathe, et al. Orientation discrimination of single-stranded DNA inside the alpha-hemolysin membrane channel. Proc Natl Acad Sci U S A. Aug. 30, 2005;102(35):12377-82. Epub Aug. 19, 2005.
Maurer, et al. Reconstitution of ion channels in agarose-supported silicon orifices. Biosens Bioelectron. May 15, 2007;22(11):2577-84. Epub Nov. 13, 2006.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci U S A. Feb. 1, 2000;97(3):1079-84.
Meller, et al. Single molecule measurements of DNA transport through a nanopore. Electrophoresis. Aug. 2002;23(16):2583-91.
Mohammad, et al. Controlling a single protein in a nanopore through electrostatic traps. J Am Chem Soc. Mar. 26, 2008;130(12)4081-8. Epub Mar. 6, 2008.
Movileanu, et al. Partitioning of a polymer into a nanoscopic protein pore obeys a simple scaling law. Proc Natl Acad Sci U S A. Aug. 28, 2001;98(18):10137-41. Epub Aug. 14, 2001.
Movileanu, et al. Partitioning of individual flexible polymers into a nanoscopic protein pore. Biophys J. Aug. 2003;85(2):897-910.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office action dated Feb. 25, 2013 for U.S. Appl. No. 13/396,522.
Office action dated Apr. 11, 2013 for U.S. Appl. No. 12/658,603.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 2, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Office action dated Nov. 26, 2011 for U.S. Appl. No. 12/308,091.
Office action dated Dec. 17, 2012 for U.S. Appl. No. 13/620,973.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Perkins, et al. Relaxation of a single DNA molecule observed by optical microscopy. Science. May 6, 1994;264(5160):822-6.
Pourmand, et al. Multiplex Pyrosequencing. Acids Res. Apr. 1, 2002;30(7):e31.
Purnell, et al. Discrimination of single base substitutions in a DNA strand immobilized in a biological nanopore. ACS Nano. Sep. 22, 2009;3(9):2533-8.
Reiner, et al. Temperature sculpting in yoctoliter volumes. J Am Chem Soc. Feb. 27, 2013;135(8):3087-94. doi: 10.1021/ja309892e. Epub Feb. 14, 2013.
Reiner, et al. Theory for polymer analysis using nanopore-based single-molecule mass spectrometry. Proc Natl Acad Sci U S A. Jul. 6, 2010;107(27):12080-5. doi: 10.1073/pnas.1002194107. Epub Jun. 21, 2010.
Rief, et al. Sequence-dependent mechanics of single DNA molecules. Nat Struct Biol. Apr. 1999;6(4):346-9.
Schneider et al. "DNA sequencing with nanopores." Nature biotechnology 30.4 (2012): 326-328.
Robertson, et al. Single-molecule mass spectrometry in solution using a solitary nanopore. Proc Natl Acad Sci U S A. May 15, 2007;104(20):8207-11. Epub May 9, 2007.
Rosenblum, et al. New dye-labeled terminators for improved DNA sequencing patterns. Nucleic Acids Res. Nov. 15, 1997;25(22):4500-4.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rotem et al., Temperature Measurement in the Intel Core Duo Processor, 2007.

(56) References Cited

OTHER PUBLICATIONS

Saleh, et al. Direct detection of antibody-antigen binding using an on-chip artificial pore. Proc Natl Acad Sci U S A. Feb. 4, 2003;100(3):820-4. Epub Jan. 27, 2003.
Sanchez-Magraner, et al. Membrane insertion of *Escherichia coli* alphahemolysin is independent from membrane lysis. J Biol Chem. Mar. 3, 2006;281(9):5461-7. Epub Dec. 22, 2005.
Sauer-Budge, et al. Unzipping kinetics of double-stranded DNA in a nanopore. Phys Rev Lett. Jun. 13, 2003;90(23):238101. Epub Jun. 9, 2003.
Seo, et al. Photocleavable fluorescent nucleotides for DNA sequencing on a chip constructed by site-specific coupling chemistry. Proc Natl Acad Sci U S A. Apr. 13, 2004;101(15):5488-93. Epub Apr. 2, 2004.
Shim, et al. Encapsulating a single G-quadruplex aptamer in a protein nanocavity. J Phys Chem B. Jul. 17, 2008;112(28):8354-60. Epub Jun. 19, 2008.
Simon, et al. Formation and stability of a suspended biomimetic lipid bilayer on silicon submicrometer-sized pores. J Colliod Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-743.
Singh, et al. Synthesis of natural flutimide and analogous fully substituted pyrazine-2,6-diones, endonuclease inhibitors of influenza virus. J Org Chem. Aug. 10, 2001;66(16):5504-16.
Smith, et al. Overstretching B-DNA: the elastic response of individual double-stranded and single-stranded DNA molecules. Science. Feb. 9, 1996;271(5250):795-9.
Stanford, et al. Transport of DNA through a single nanometer-scale pore: evolution of signal structure. IEEE Workshop on Genomic Signal Processing and Statistics. Baltimore, MD. May 26, 2004.
Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.
Stefureac, et al. Nanopore analysis of the interaction of metal ions with prion proteins and peptides. Biochem Cell Biol. Apr. 2010;88(2):347-58.
Stefureac, et al. Transport of alpha-helical peptides through alpha-hemolysin and aerolysis pores. Biochemistry. Aug. 1, 2006;45(30):9172-9.
Stoddart, et al. Nucleobase recognition in ssDNA at the central constriction of the alpha-hemolysin pore. Nano Lett. Sep. 8, 2010;10(9):3633-7.
Stoddart, et al. Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.
Storm, et al. Translocation of double-strand DNA through a silicon oxide nanopore. Phys Rev E Stat Nonlin Soft Matter Phys. May 2005;71(5 Pt 1):051903. Epub May 6, 2005.
Streater, et al. Novel 3-hydroxy-2(1H)-pyridinones. Synthesis, iron(III)-chelating properties, and biological activity. J Med Chem. Jun. 1990;33(6):1749-55.
Studer, et al. Formation of individual protein channels in lipid bilayers suspended in nanopores. Colloids Surf B Biointerfaces. Oct. 15, 2009;73(2):325-31. Epub Jun. 10, 2009.
Suzuki, et al. Highly reproducible method of planar lipid bilayer reconstitution in polymethyl methacrylate chip. Langmuir. Feb. 14, 2006;22(4):1937-42.

Thomson et al. Preliminary nanopore cheminformatics analysis of aptamer-target binding strength. BMC Bioinformatics. Nov. 1, 2007;8 Suppl 7:S11.
UK search and examination report dated Feb. 25, 2013 for GB Application No. 1216656.7.
UK search and examination report dated May 1, 2013 for GB Application No. 1216026.3.
U.S. Appl. No. 13/918,626 (published as US20140034497A1 on Feb. 6, 2014).
Vercoutere, et al. Discrimination among individual Watson-Crick base pairs at the termini of single DNA hairpin molecules. Nucleic Acids Res. Feb. 15, 2003;31(4):1311-8.
Vercoutere, et al. Rapid discrimination among individual DNA hairpin molecules at single-nucleotide resolution using an ion channel. Nat Biotechnol. Mar. 2001;19(3):248-52.
Viasnoff, et al. Probing DNA base pairing energy profiles using a nanopore. Eur Biophys J. Feb. 2009;38(2):263-9. Epub Oct. 3, 2008.
Wang, et al. DNA heterogeneity and phosphorylation unveiled by single-molecule electrophoresis. Proc Natl Acad Sci U S A. Sep. 14, 2004;101(37):13472-7. Epub Sep. 1, 2004.
Wanunu, et al. DNA profiling using solid-state nanopores: detection of DNA-binding molecules. Nano Lett. Oct. 2009;9(10):3498-502.
Weng, et al. Fluid biomembranes supported on nanoporous aerogel/xerogel substrates. Langmuir. Aug. 17, 2004;20(17):7232-9.
Wilson, et al. Electronic control of DNA polymerase binding and unbinding to single DNA molecules. ACS Nan. Apr. 28, 2009;3(4):995-1003.
Wilson, et al. Feedback control of a DNA molecule tethered in a nanopore to repeatedly probe DNA-binding enzymes. Conf Proc IEEE Eng Med Biol Soc. 2008;2008:5745-8.
Winters-Hilt, et al. Nanopore-based kinetics analysis of individual antibody-channel and antibody-antigen interactions. BMC Bioinformatics. Nov. 1, 2007;8 Suppl 7:S20.
Woodside, et al. Direct measurement of the full, sequence-dependent folding landscape of a nucleic acid. Science. Nov. 10, 2006;314(5801):1001-4.
Woodside, et al. Nanomechanical measurements of the sequence-depepndent folding landscapes of single nucleic acid hairpins. Proc Natl Acad Sci U S A. Apr. 18, 2006;103(16):6190-5. Epub Apr. 10, 2006.
Wu, et al. Single-molecule detection of nitrogen mustards by covalent reaction within a protein nanopore. J Am Chem Soc. May 28, 2008;130(21):6813-9. Epub Apr. 30, 2008.
Zeineldin, et al. Using bicellar mixtures to form supported and suspended lipid bilayers on silicon chips. Langmuir. Sep. 12, 2006;22(19):8163-8.
Zwolak, et al. Electronic signature of DNA nucleotides via transverse transport. Nano Lett. Mar. 2005;5(3):421-4.
Molloy et al., Automation of Biochip Array Technology for Quality Results, Clin Chem Lab Med, 2005.
Venkatesan et al., Nanopore Sensors for Nucleic Acid Analysis, Nature Nanotechnology, vol. 6, No. 10, pp. 615 Sep. 18, 2011.
Timp et al., Nanopore Sequencing: Electrical Measurements of the Code of Life, IEEE Transactions on Nanotechnology, vol. 9, No. 3, May 2010.
Rosenstein et al., Nanopore DNA Sensors in CMOS with On-Chip Low-Noise Preamplifiers, 2011 16th International Solid-State Sensors, Actuators and Microsystems Conference, Jun. 5-9, 2011.
Nakane et al., Nanopore Sensors for Nucleic Acid Analysis, Journal of Physics, Condensed Matter 15.32, Aug. 1, 2003, R1365.

\* cited by examiner

SYSTEM FOR COMMUNICATING INFORMATION FROM AN ARRAY OF SENSORS

CROSS REFERENCE TO OTHER APPLICATIONS

This application claims priority to U.S. Provisional Patent Application No. 61/435,700 entitled SYSTEM FOR COMMUNICATING INFORMATION FROM AN ARRAY OF SENSORS filed Jan. 24, 2011 which is incorporated herein by reference for all purposes.

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips.

BRIEF DESCRIPTION OF THE DRAWINGS

Various embodiments of the invention are disclosed in the following detailed description and the accompanying drawings.

DETAILED DESCRIPTION

Figure 1:
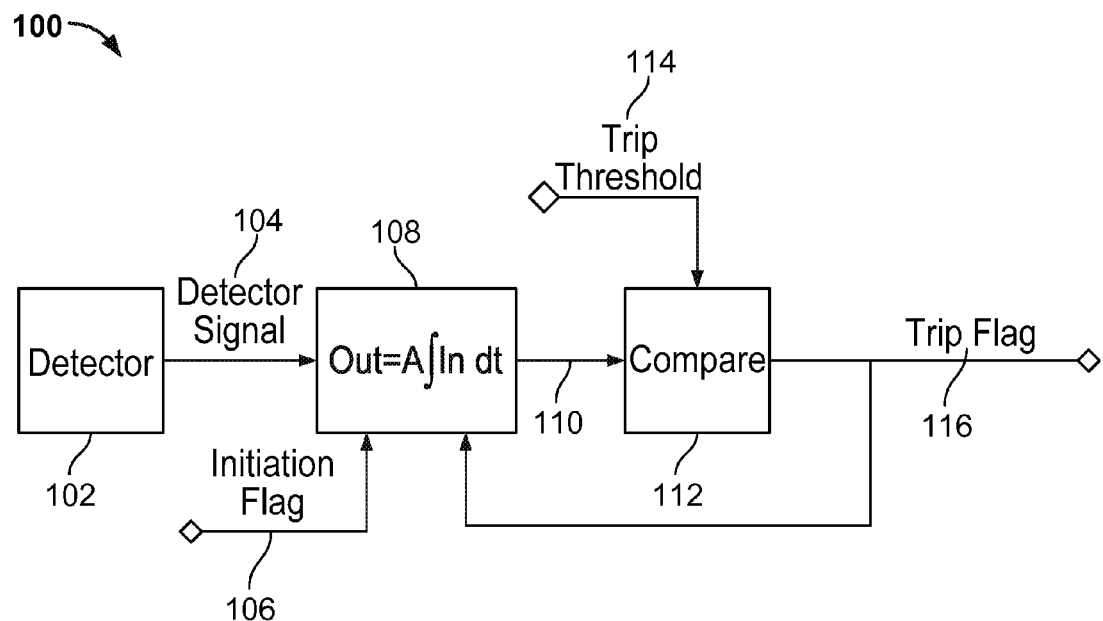
FIG. 1 is a block diagram illustrating an embodiment of a signal processing and sensor circuitry 100 for measuring a physical property within a single cell in a biochip.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore and a single strand of DNA, and anything bound to that single strand of DNA. The nanopore is a small hole in an electrically insulating membrane that can be used as a single-molecule detector. A nanopore may be formed using a biological material, such as α-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting the electrical patterns, or signatures, of a molecule passing through the nanopore. In order to reduce the cost of the array, physically small single cells with highly sensitive sensors therein are desirable.

FIG. 1 is a block diagram illustrating an embodiment of a signal processing and sensor circuitry 100 for measuring a physical property within a single cell in a biochip. As shown in FIG. 1, a physical property, e.g., a current, voltage, or charge, is detected by detector 102 as detected signal 104.

Signal processing and sensor circuitry 100 may be used to measure the mean value of detected signal 104 without sampling as described further below.

In some embodiments, an initiation flag 106 resets an integrating amplifier 108 and starts a continuous integration of detected signal 104 over time. Integrated output 110 is compared with a trip threshold 114 using a comparator 112. When integrated output 110 reaches trip threshold 114, a trip flag 116 may be used as a feedback signal to integrating amplifier 108 for terminating the integration of detected signal 104. For example, when trip flag 116 is "on" or asserted, the integration is terminated. The duration of time between the assertion of initiation flag 106 and the assertion of trip flag 116 is proportional to the mean value of detected signal 104, e.g., the mean value of a current. Accordingly, the "on" and "off" of trip flag 116 (only 1 bit of information) may be sent from the cell to an external processor for calculating the mean value of detected signal 104. Alternatively, the "on/off" information may be sent from the cell to an external storage for delayed processing. For example, the clock cycles at which initiation flag 106 and trip flag 116 are respectively asserted may be recorded in an external storage. The number of clock cycles between the two asserted flags may then be used to determine the mean value of detected signal 104 at a later time.

In some embodiments, more accurate results may be obtained by integrating detected signal 104 over multiple integrating cycles. For example, the determined mean value of detected signal 104 may be further averaged over multiple integrating cycles. In some embodiments, initiation flag 106 is based at least in part on trip flag 116. For example, initiation flag 106 may be re-asserted in response to trip flag 116 being asserted. In this example, trip flag 116 is used as a feedback signal for reinitializing integrating amplifier 108, such that another cycle of integration of detected signal 104 may begin as soon as the previous cycle of integration is terminated. Re-asserting initiation flag 106 immediately after trip flag 116 is asserted reduces the portion of time when detector 102 generates a signal that is not integrated and thus not measured. The integration occurs over approximately the entire time that the signal is available. As a result, most of the information of the signal is captured, thereby minimizing the time to obtain an average value for the measured signal.

Shot noise may corrupt trip flag 116 during certain integrating cycles. Accordingly, some embodiments may include logic to determine whether trip flag 116 has been corrupted by shot noise in a particular integrating cycle before trip flag 116 is saved or used for any calculation.

Figure 2:
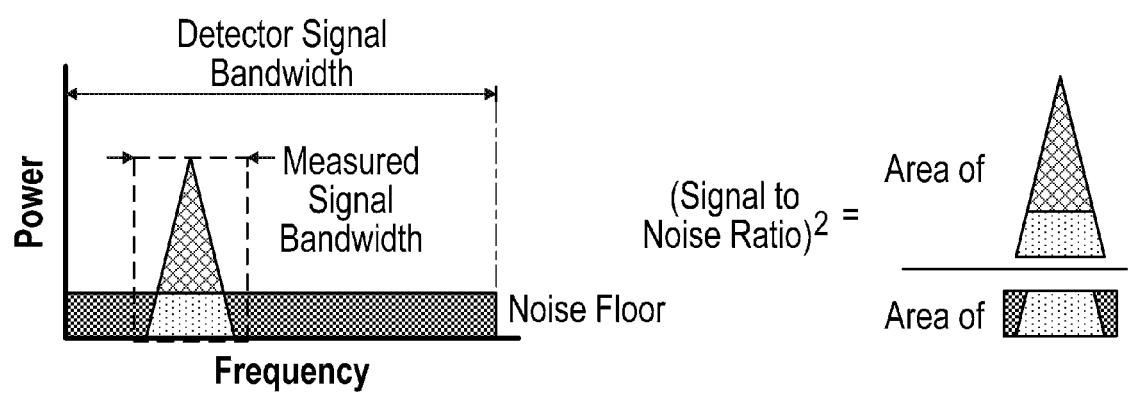
FIG. 2 illustrates that with a constant noise floor, as the measured signal bandwidth decreases, the signal to noise ratio increases, thereby improving the sensitivity of sensor circuit 100 of FIG. 1.

The sensitivity of sensor circuit 100 is maximized by continuously integrating detected signal 102 without sampling. This serves to limit the bandwidth of the measured signal. With continuous reference to FIG. 1, trip threshold 114 and an integration coefficient A set the bandwidth of the measured signal. As integration coefficient A decreases or as trip threshold 114 increases, the measured signal bandwidth decreases. FIG. 2 illustrates that with a constant noise floor, as the measured signal bandwidth decreases, the signal to noise ratio increases, improving the sensitivity of sensor circuit 100. In some embodiments, the measured signal bandwidth can be dynamically adjusted by varying the trip threshold 114.

Figure 3:
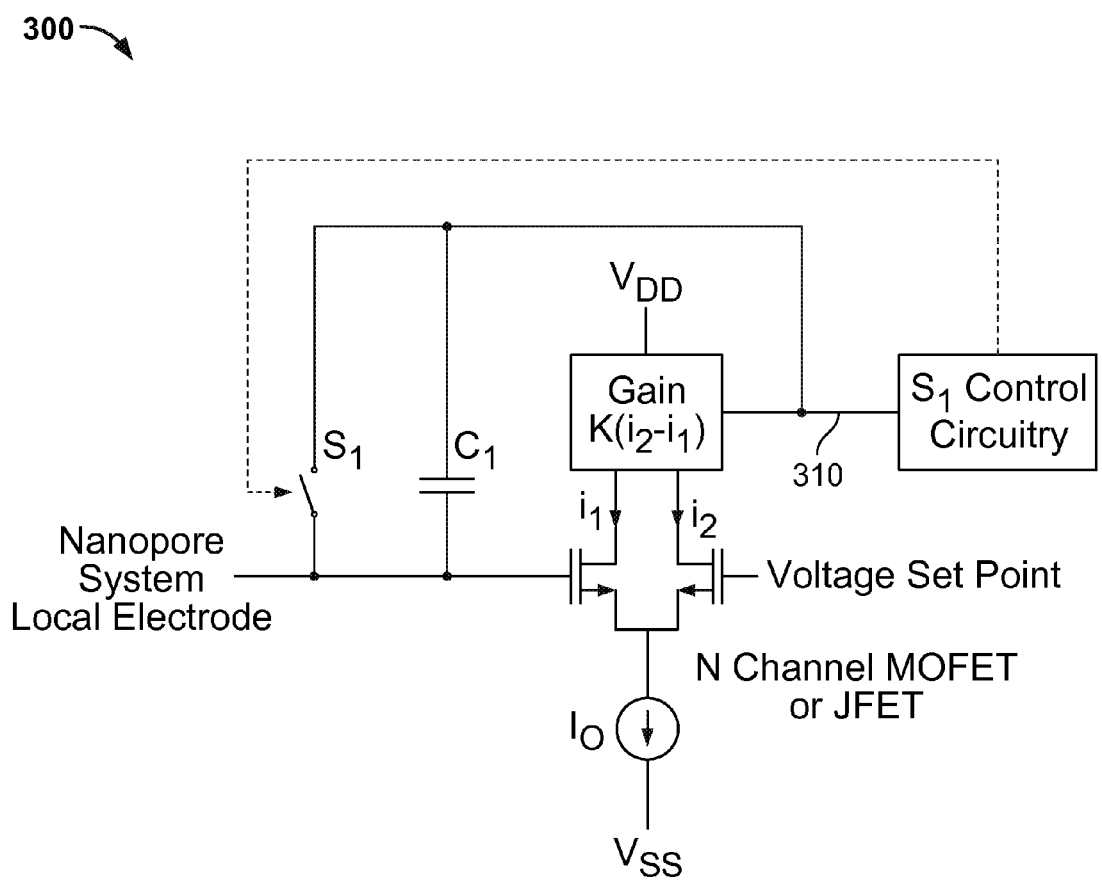
FIG. 3 is a circuit diagram illustrating an embodiment of a signal processing and sensor circuitry 300 for measuring a physical property, e.g., a current, within a single cell in a nanopore array.
Figure 4:
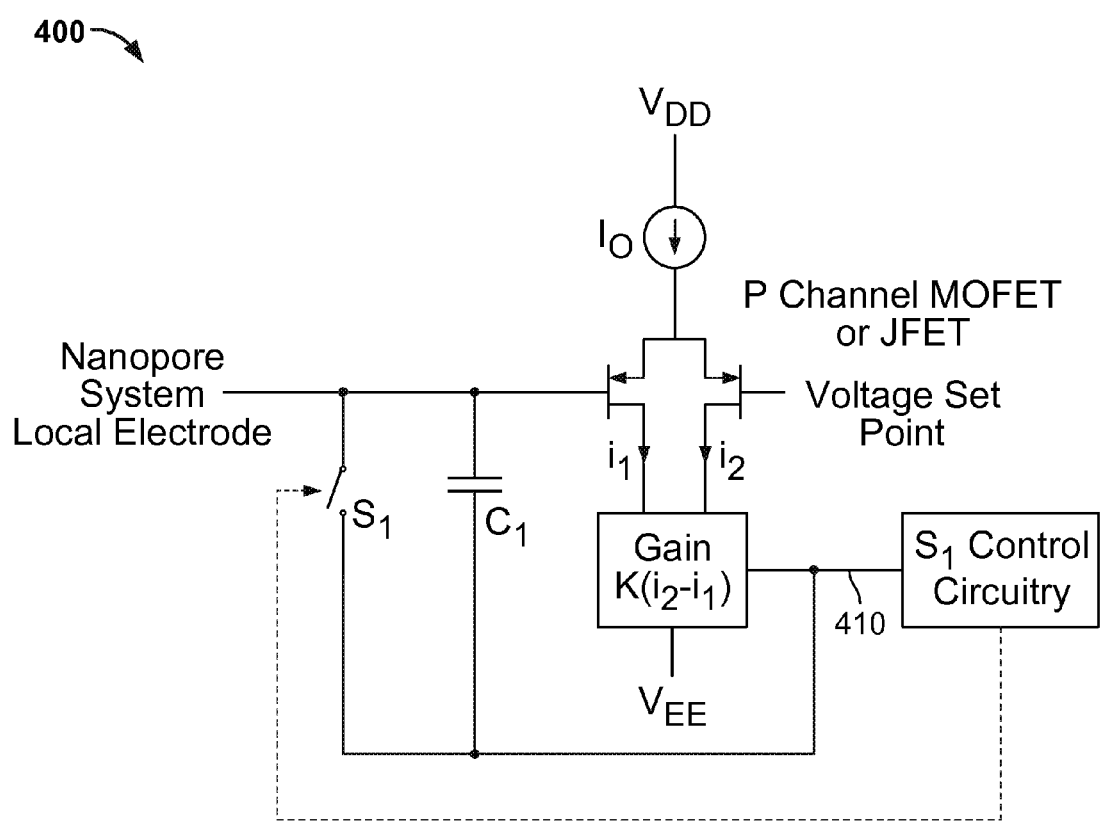
FIG. 4 is a circuit diagram illustrating a second embodiment of a signal processing and sensor circuitry 400 for measuring a physical property within a single cell in a nanopore array.

FIG. 3 is a circuit diagram illustrating an embodiment of a signal processing and sensor circuitry 300 for measuring a physical property, e.g., a voltage, within a single cell in a nanopore array. FIG. 4 is a circuit diagram illustrating a second embodiment of a signal processing and sensor circuitry 400 for measuring a physical property within a single cell in a nanopore array.

With reference to FIGS. 3 and 4, the S1 control circuitry includes a comparator and other logic, e.g., logic for switching. The other components of circuit 300 (or circuit 400), including the differential pair, implement an integrating amplifier similar to that in FIG. 1. The input of circuit 300 (or circuit 400) is connected to a nanopore system local electrode.

Figure 5:
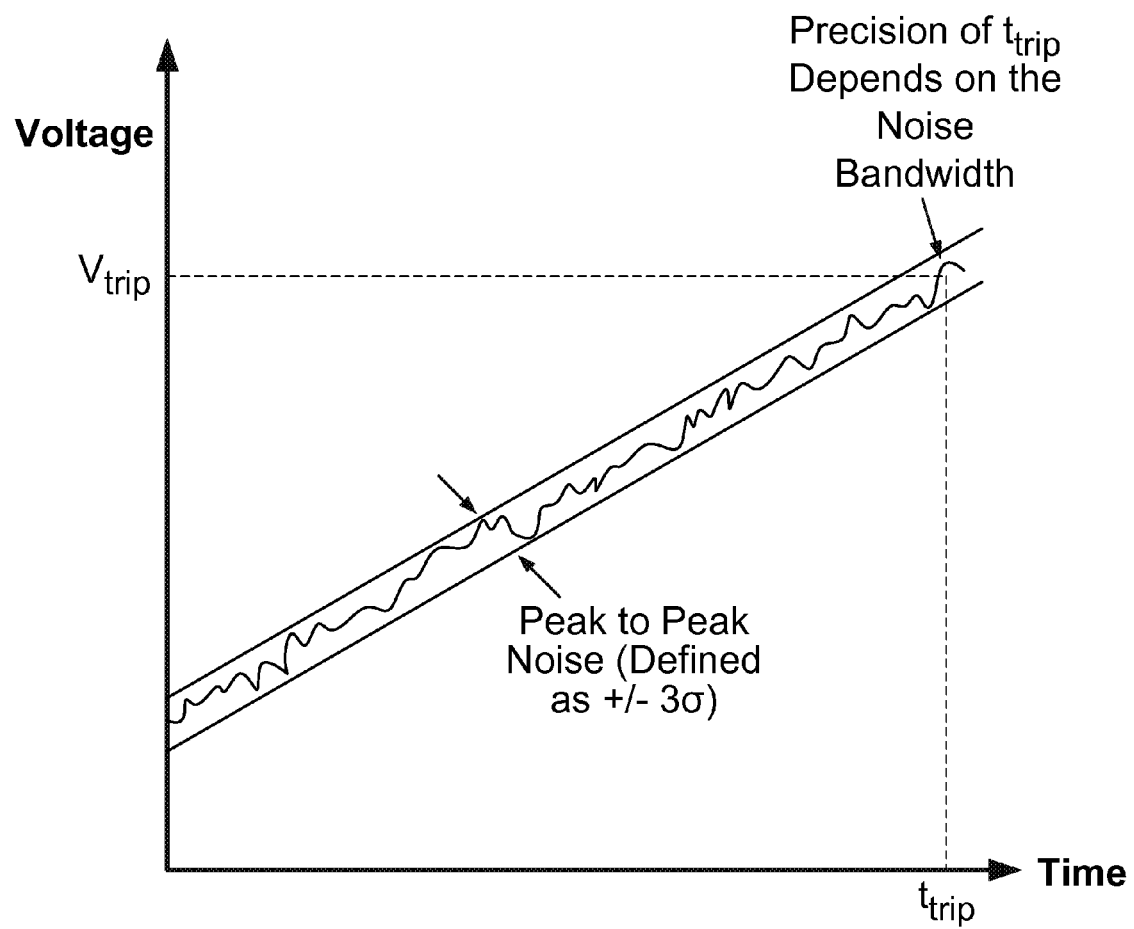
FIG. 5 is a diagram illustrating a plot of the voltage at the output of the integrating amplifier in circuit 300 or circuit 400 versus time.

FIG. 5 is a diagram illustrating a plot of the voltage at 310 (or 410) in circuit 300 (or circuit 400) versus time. In FIG. 5, $t_{trip}$ indicates the mean current flowing through a nanopore. Reducing the noise bandwidth reduces the noise associated with $t_{trip}$. Accordingly, the mean current measurement will have a higher signal to noise ratio (SNR) and be more precise.

The integrating amplifier is configured to amplify only the in-band signal, but not the out-of-band signal. Amplifying all signals amplifies mostly noise since the useful signal's bandwidth is much smaller than the detected signal, resulting in poor SNR. The noise bandwidth may be limited by selecting appropriate values for $C_1$ and $I_O$ in circuits 300 and 400. In some embodiments, $C_1$ and $I_O$ are selected to limit the noise bandwidth between 0.3 Hz and 300 Hz. In some embodiments, the noise bandwidth can be dynamically adjusted by varying the values of $C_1$.

In some embodiments, trip flag 116 for each of the cells are further synchronized with a global clock shared by all the cells within the biochip. For example, trip flag 116 that is synchronized with a global clock may be generated by a pulse generation circuit. After synchronization, trip flag 116 is a single pulse that is in phase with the global clock.

Figure 6:
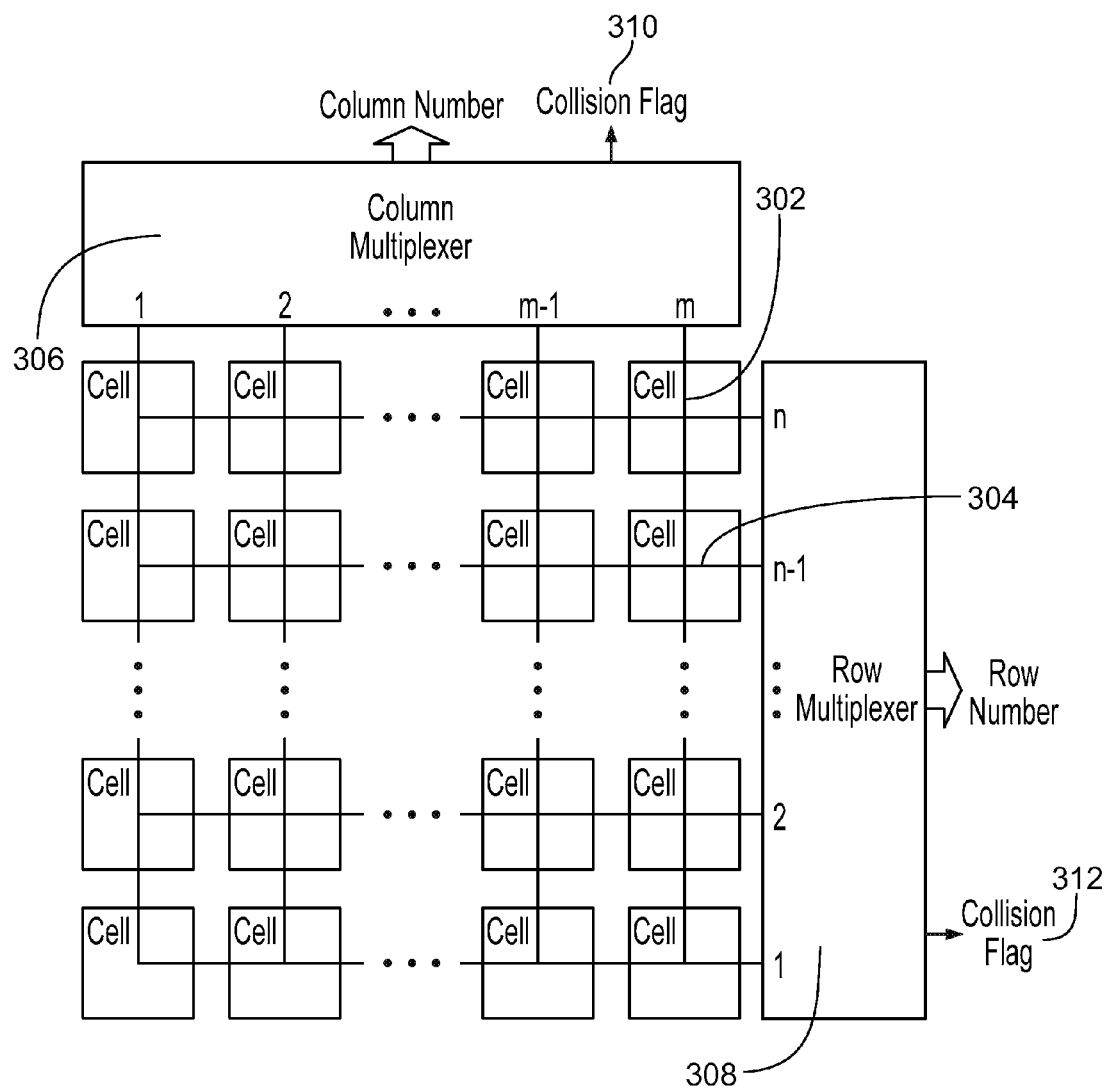
FIG. 6 is a block diagram illustrating an embodiment of a cell array in a biochip.

FIG. 6 is a block diagram illustrating an embodiment of a cell array in a biochip. Each of the cells may contain a sensor circuit 100 for measuring a physical property within the cell as described above. As shown in FIG. 6, the cell array has m columns by n rows of single cells. All the cells in a given column share the same column line 302, and all the cells in a given row share the same row line 304. When trip flag 116 for a particular cell is asserted, the cell asserts its particular column line 302 and row line 304. In order to reduce the pin count of the biochip, a column multiplexer 306 may be used to output a column number ($0-2^m-1$) to indicate which column line 302 has been asserted. Similarly, a row multiplexer 308 may be used to output a row number ($0-2^n-1$) to indicate which row line 304 has been asserted. For example, if trip flag 116 of the cell in the second column and the second row is asserted, the output column and row number is (1, 1). As long as only one cell asserts its trip flag 116 at a time, the reported column and row numbers are sufficient to uniquely identify which particular cell is asserted at a particular time.

The above techniques have a number of advantages over other approaches. The integrating amplifier requires minimal die area and allows for each array site to have its own dedicated measurement circuit. This feature removes the necessity of routing sensitive analog signals to the array periphery and avoids the need for multiplexing, thereby reducing noise. The integrating amplifier requires no pre-amplifier, sample and hold, or anti-aliasing filter, further reducing die area and potential error sources. Since only a single flag is required to denote the completion of a measurement, the integrating approach is an efficient way to communicate data from each array site. Measurements are being made continuously (other than the brief time required to reset the integration capacitor) so data is being gathered almost 100% of the time. Furthermore, each cell and its associated measurement circuit operate autonomously, allowing each cell to track the state of the molecule being measured. As described above, the integrating approach also has inherent signal averaging and noise advantages.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for communicating information from a nanopore sensor array, comprising:
   a nanopore sensor array including a plurality of nanopore sensors, wherein each sensor senses a physical property of a material that is in communication with the sensor;
   signal processing circuitry associated with each sensor that integrates the output of the sensor over time and compares the integrated output to a threshold; and
   a communication network coupled to the signal processing circuitry that outputs information indicating that the integrated output corresponding to a given sensor has reached the threshold, wherein the information comprises a 1-bit flag; and
   wherein the sensor array comprises a first plurality of rows of sensors and a second plurality of columns of sensors, and wherein the 1-bit flags for each row of sensors share a row signal line, and wherein the 1-bit flags for each column of sensors share a column signal line, and wherein each row signal line is asserted in the event that at least one 1-bit flag sharing the row signal line is asserted, and wherein each column signal line is asserted in the event that at least one 1-bit flag sharing the column signal is asserted.

2. The system of claim 1, wherein integrating the output of the sensor over time comprises initiating the integration based on an initiation flag and terminating the integration based on the information indicating that the integrated output corresponding to the sensor has reached the threshold.

3. The system of claim 2, wherein the communication network further outputs a state of the initiation flag.

4. The system of claim 2, wherein a time period between the initiating and the terminating of the integration corresponds to a mean value of the physical property.

5. The system of claim 2, wherein integrating the output of the sensor over time is repeated by deriving the initiation flag based at least in part on the information indicating that the integrated output corresponding to the sensor has reached the threshold.

6. The system of claim 5, wherein the initiation flag is re-asserted in response to the information indicating that the integrated output corresponding to the sensor has reached the threshold.

7. The system of claim 1, wherein a bandwidth of the integrated output is adjusted based at least in part on adjusting a coefficient associated with the signal processing circuitry.

8. The system of claim 1, wherein a bandwidth of the integrated output is adjusted based at least in part on adjusting the threshold.

9. The system of claim 1, wherein a bandwidth of the integrated output is adjusted based at least in part on adjusting a capacitance associated with the signal processing circuitry.

10. The system of claim 1, wherein a signal to noise ratio of the integrated output is increased based at least in part on reducing a bandwidth of the integrated output.

11. The system of claim 1, wherein the physical property comprises one of the following: a current, voltage, or charge.

12. The system of claim 1, wherein the information corresponds to a mean value of the physical property.

13. The system of claim 1, wherein the 1-bit flag for a given sensor is synchronized with a global clock shared by the plurality of sensors.

14. The system of claim 13, wherein the 1-bit flag is generated by a pulse generation circuit.

15. The system of claim 1, further comprising a row multiplexer that outputs a row number in response to an asserted row signal line, the row number corresponding to the asserted row signal line.

16. The system of claim 1, further comprising a column multiplexer that outputs a column number in response to an asserted column signal line, the column number corresponding to the asserted column signal line.

17. A method for communicating information from a nanopore sensor array, comprising
   sensing a physical property of a material that is in communication with each sensor in a nanopore sensor array;
   integrating the output of each sensor over time and comparing the integrated output to a threshold; and
   outputting information indicating that the integrated output corresponding to a given sensor has reached the threshold, wherein the information comprises a 1-bit flag; and
   wherein the sensor array comprises a first plurality of rows of sensors and a second plurality of columns of sensors, and wherein the 1-bit flags for each row of sensors share a row signal line, and wherein the 1-bit flags for each column of sensors share a column signal line, and wherein each row signal line is asserted in the event that at least one 1-bit flag sharing the row signal line is asserted, and wherein each column signal line is asserted in the event that at least one 1-bit flag sharing the column signal is asserted.

\* \* \* \* \*